United States Patent [19]

Whitcomb

[11] Patent Number: Plant 6,365

[45] Date of Patent: Nov. 1, 1988

[54] CRAPE MYRTLE

[75] Inventor: Carl E. Whitcomb, Stillwater, Okla.

[73] Assignee: Oklahoma State University, Stillwater, Okla.

[21] Appl. No.: 791,078

[22] Filed: Sep. 23, 1985

[51] Int. Cl.[4] ..... A01H 5/00

[52] U.S. Cl. ..... Plt./54

[58] Field of Search ..... Plt./54

*Primary Examiner*—Robert E. Bagwill

*Attorney, Agent, or Firm*—Head & Johnson

[57] ABSTRACT

A compact, upright and semi-dwarf crape myrtle which bears a variegated pink flower bordered by pure white over an extremely long period of time.

2 Drawing Sheets

BACKGROUND OF THE INVENTION

1. Field of the Invention:

The present invention relates to a new and distinct variety of cultivar of the ornamental shrub, *Lagerstroemia indica,* commonly known as crape myrtle.

2. Description of the Prior Art:

Most crape myrtle seedlings and cultivars flower early in the summer, set heavy seed crop and then flower sparsely the remainder of the growing season. Various attempts to develop improved varieties of the crape myrtle have been pursued commercially, including the issuance of several U.S. plant patents. For example, U.S. Plant Pat. Nos. 4,182 through 4,185 disclose and claim a series of four new varieties of *Lagerstroemia indica* produced by crossing unnumbered or unnamed seedlings. Each of these new varieties was characterized as having a weeping growth habit at full maturity. Also, U.S. Plant Pat. No. 4,189 discloses a new variety of crape myrtle produced by crossing seed parent SL blue (color 1–13) with pollen parent XX 224 blue star-shaped (color 1–13) and again, exhibiting a weeping growth habit at full maturity. In U.S. Plant Pat. No. 2,551, a dwarf habit hybrid of *Lagerstroemia indica* and *Lagerstroemia reginae* was disclosed and claimed.

It is generally known that ethylmethane sulfonate, EMS, is capable of producing mutant growth in plants. EMS frequently induces sterility in the plant mutant and the mutants often have thicker than normal leaves and variegated flowers, with an occasional flower that is a solid color among the predominantly variegated flowers. The new variety of crape myrtle of the present invention is such a mutant.

SUMMARY OF THE INVENTION

I have discovered a new and distinct variety of crape myrtle, *Lagerstroemia indica,* which is characterized by a compact, upright, semi-dwarf shrub that may reach 1.2 to 2 m in height. The leaves of the plant are smaller and thicker than the species average and are very dark green. Inflorescences are 12 to 25 cm tall and 8 to 12 cm wide. Individual petals are medium pink bordered by pure white.

BRIEF DESCRIPTION OF THE DRAWINGS

A plant of the new variety is shown in full color in the accompanying photographs.

FIG. 1 is a view in full color showing the general form and arrangement of a typical bush or full plant.

FIG. 2 is a view in full color showing the flower head and leaves of a fully matured, flowered plant.

DESCRIPTION OF THE VARIETY

The new variety of crape myrtle was selected from a population derived from about 4,000 seeds collected from 16 seedling parents and treated with a 4 percent solution of ethylmethane sulfonate, EMS. Treated seeds were planted in flats in the greenhouse. After the seed germinated, powdery mildew was introduced from susceptible seedlings in large containers. About 1,200 seedlings showed resistance to mildew and were transplanted into the field for further evaluation. The new plant was among 60 seedlings selected for good form and flowering characteristics. It is probably a mutant arising from the EMS treatment. EMS is known to frequently induce sterility, and mutants induced from EMS often have thicker than normal leaves with variegated flowers with an occasional flower that is a solid color among the predominantly variegated flowers. Such characteristics have been observed in this new variety of crape myrtle.

Soft wood cuttings taken from the original parent have been successfully rooted (100 percent) in a medium of peat and perlite under intermittent mist. Subsequent cuttings taken from plants resulting from previous cuttings have been similarly rooted. Growth and flowering of the rooted plants remain consistent with the parent. The plant does not reproduce from seed.

A detailed description of the new variety of crape myrtle follows:

Parentage: Selected from 4,000 common crape myrtle seeds, treated with ethylmethane sulfonate to induce mutations. The thick leathery leaves, variegated flowers, long bloom time, and near sterility, are all indications that the new variety is a mutant.

Growth: The plant is a compact, upright semi-dwarf shrub that may reach 1.2 to 2 m in height with age. Growth is slow since little growth occurs after the photoperiod triggers flowering in mid to late June.

Branches: The plant branches moderately, but remains upright in basic form.

Foliage: Leaves are smaller and thicker than species average, typically 4 to 5 cm wide and 5 to 9 cm long at full maturity. New leaves emerge wine-red (the color varies with light intensity and growing condition) gradually turning very dark green (emerald green #758; color notations are from The Royal Horticultural Society Colour Chart).

Flowers: Individual petals are pink (Rose madder, #23; Royal Horticultural Society) bonded by pure white on the outer margin. The width of the white margin varies slightly with the temperature and growing conditions, but is always present. The presence of flowers of different ages, thus developed under slightly different temperature conditions, gives the plant a unique appearance due to the variation in flower color. Inflorescences are 12 to 25 cm tall and 8 to 12 cm wide and are comprised of a plurality of flower heads varying typically from about 3 cm to 5 cm or larger.

The new variety begins flowering in mid-June and continues through late September. This period is much longer than seen for most seedlings and cultivars of crape myrtle. Flowering continues during droughts and periods of prolonged heat. Seeds set is very light, which accounts for the extended flowering. The flower has shown consistent resistance to powdery mildew, both in the landscape and under conditions of daily overhead watering in containers. It has withstood temperatures of 20° C. on several occasions with no dieback of the type frequently occurring with many cultivars and seedlings.

I claim:

1. A new and distinct variety of *Lagerstroemia indica* plant substantially as shown and described and particularly characterized by a compact, upright and semi-dwarf growth habit, a variegated flower having individual petals of pink, Rose madder #23, bordered by pure white on the outer margin, dark green leathery leaves and an exceptionally long bloom period.

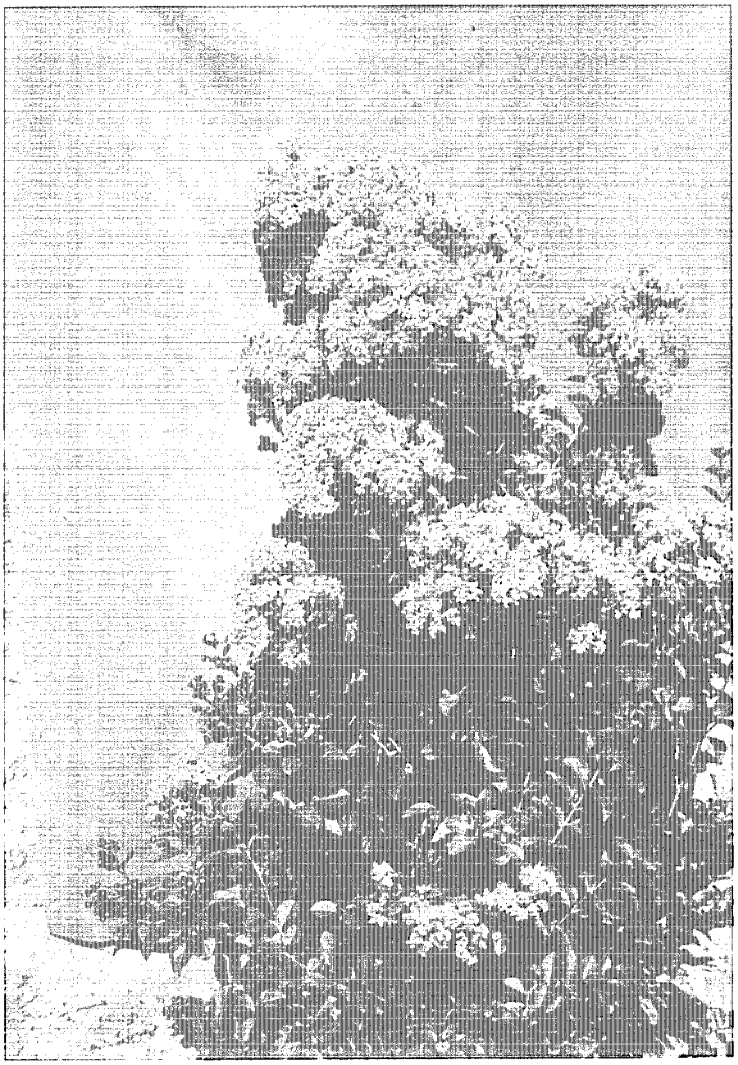

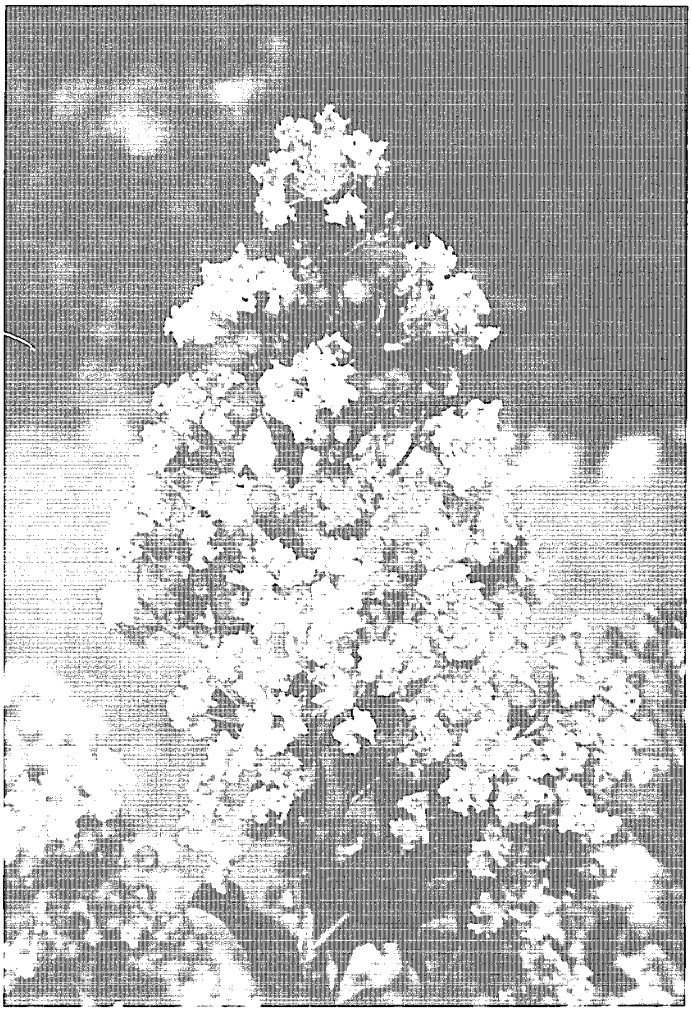

* * * * *